(12) United States Patent
Guram

(10) Patent No.: US 6,225,487 B1
(45) Date of Patent: *May 1, 2001

(54) ANCILLARY LIGANDS AND METAL COMPLEXES, CATALYSTS AND COMPOSITIONS USING SAME AND METHODS OF TESTING

(75) Inventor: Anil Guram, Sunnyvale, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/062,128

(22) Filed: Apr. 17, 1998

(51) Int. Cl.$^7$ .............. C07F 9/28; C07F 19/00; C07D 321/00; C07D 307/02

(52) U.S. Cl. .............. 556/18; 549/200; 549/491; 549/497; 556/21; 568/2; 568/6; 568/13; 568/17

(58) Field of Search .............. 549/200, 491, 549/497; 568/2, 6, 13, 17; 556/18, 21

(56) References Cited

FOREIGN PATENT DOCUMENTS

| 2239970A | 6/1997 | (CA) . |
| WO 93/12260 | 6/1993 | (WO) . |
| WO 99/54337 | 10/1999 | (WO) . |

OTHER PUBLICATIONS

Chemical Abstract vol. 131, 1999 12–07 No. 2 (abstract of Organometallics, 1999 18 (10) 1840–1853).
Chemical Abstract vol. 124 (1996) 09–04 No. 15 (abstract of Bull. Korean Chem. Soc. 1995 16(12) 1135–8).
Shirakawa E., May 26, 1997, Tetrahedron Letters 38 (21): 759–3762 "An Iminophosphine–palladium catalyst for cross–coupling of aryl halides with organostannanes".
Horner, L., 1984, Zeitschrift Fur Naturforschung, Teil B : Anorganische Chemie, Organische Chemie., 39 (4) : 504–511 "Tertiare Phosphine mit ortho–standigen chelatisierungsfahigen funktionellen Gruppen als Co–Katalysatoren der Homogenhydrierung mit Rh(l)–Komplexen".
Trofimov B.A., 1995, Synthesis 4: 387–388 "Base–catalyzed addition of phosphine to aryl– and hetarylethynes".
Kamikawa, K., Nov. 13, 1998, J. Org. Chem. 63 (23): 8407–8410 "Palladium–Catalyzed Amination of Aryl Bromides Utilizing Arene–Chromium Complexes as Ligands".
Bei, Xiaohong et al., 1999, Tetrahederon Letters 40: 1237–1240 General and Efficient Palladium–Catalyzed Aminations of Aryl Chlorides.
Hellwinkel, Dieter., et al., "Polycyclic triaryldioxyphosphoranes of extreme stability," *Chem. Bur.*, vol. 111, pp. 13–41, 1978.
Hoots, John E., et al., "Substituted triaryl phosphines," *Inorg. Synth.*, vol. 21, pp. 175–179, 1982.

Vaughn, George D., et al., "Synthesis and reactivity of stable metallacyclic manganese and rhenium α–hydroxyalkyl complexes of the formula [cyclic] $(CO_4MP(C_6H_5)_2(o-C_6H_4CHOH))$," *J. Am. Chem. Soc.*, vol. 108, pp. 1462–1473, 1986.

Frost, Christopher G., et al., "Enantiomerically pure acetals as ligands for asymmetric catalysis," *Synlett*, Issue 7, pp. 551–552, 1994.

Newman, Louise M., et al., "Rhodium catalysed asymmetric hydrosilylation of ketones using phosphorus–containing oxazoline ligands," *Tetrahedron: Asymmetry*, vol. 7, No. 6, pp. 1597–1598, 1996.

Grotjahn D.B., et al., "Ruthenium alkoxycarbene complexes from an acetal function by C–O bond cleavage and alcohol elimination," *Organometallics*, vol. 15, pp. 2860–2862, 1996.

Pian–pian, Xu, et al., "Synthesis, structure and hydrogenation property of $trans-PdCl_2\{Ph_2P[o-C_6H_4CH(OC_2H_5)_2]\}_2$," *Chem. Res. Chin. Univ.*, vol. 13, No. 4, pp. 397–400, 1997.

Pian–pian, Xu, et al., "Synthesis, characterization of new palladium complexes and their catalytic properties in hydrogenation reaction," *Journal of Xiamen University*, vol. 37, No. 1, pp. 52–57, 1998.

Meyers, Harold V., et al. "Multiple simultaneous synthesis of phenolic libraries," *Molecular Diversity*, vol. 1, pp. 13–20, (1995).

Meyers, Harold, V., et al. "Versatile method for parallel synthesis," *Methods in Molecular and Cellular Biology*, vol. 6, pp. 1–7, (1996).

Schiemenz, Günter P., et al. "Aromatic Phosphines with Second Order Substituents, XIII. —Preparation of Tri-arylphosphines with Several Carbonyl Functions by Grignard Synthesis," *Liebigs Ann. Chem.*, pp. 1480–1493, (1973).

Terfort, Andreas, et al. "Phosphane Ligands with Two Binding Sites of Differing Hardness for Enantioselective Grignard Cross Coupling," *J. Chem. Soc., Perkin Trans.* 1, pp. 1467–1479, (1996).

*Primary Examiner*—Porfirio Nazario-Gonzalez

(57) ABSTRACT

A new ligand having a backbone comprised of PCCC, where the last carbon atom is sp$^3$ hybridized can be combined with a metal or metal precursor compound or formed into a metal-ligand complex to catalyze a number of different chemical transformations, including C—N bond formation.

62 Claims, No Drawings

ANCILLARY LIGANDS AND METAL COMPLEXES, CATALYSTS AND COMPOSITIONS USING SAME AND METHODS OF TESTING

FIELD OF THE INVENTION

The present invention relates to new organic compounds, their metal complexes and compositions using those compounds; the invention also generally relates to the field of catalysis. In particular, this invention relates to new compounds which when combined with suitable metals or metal precursor compounds provide useful catalysts for various bond-forming reactions, including C—N bond formation. The invention also relates to combinatorial chemistry in that combinatorial techniques were used in connection with creating the ligands and testing compositions containing the ligands.

BACKGROUND OF THE INVENTION

Ancillary (or spectator) ligand-metal coordination complexes (e.g., organometallic complexes) and compositions are useful as catalysts, additives, stoichiometric reagents, monomers, solid state precursors, therapeutic reagents and drugs. Ancillary ligand-metal coordination complexes of this type can be prepared by combining an ancillary ligand with a suitable metal compound or metal precursor in a suitable solvent at a suitable temperature. The ancillary ligand contains functional groups that bind to the metal center(s), remain associated with the metal center(s), and therefore provide an opportunity to modify the steric, electronic and chemical properties of the active metal center(s) of the complex.

Certain known ancillary ligand-metal complexes and compositions are catalysts for reactions such as oxidation, reduction, hydrogenation, hydrosilylation, hydrocyanation, hydroformylation, polymerization, carbonylation, isomerization, metathesis, carbon-hydrogen activation, carbon-halogen activation, cross-coupling, Friedel-Crafts acylation and alkylation, hydration, dimerization, trimerization, oligomerization, Diels-Alder reactions and other transformations.

One example of the use of these types of ancillary ligand-metal complexes and compositions is in the field of homogeneous catalysis to form a $sp^2$ C—N bond. A $sp^2$ C—N bond is a structural component in a variety of synthetic and naturally occurring biologically active compounds, polymers and dyes. Currently, existing methodologies are not general, in that different complexes or compositions are used for different substrates. Also, existing ligands are expensive. Thus there is a need for new, less expensive ligands that are generally applicable to all types of C—N bond formation, including $sp^2$ C—N bond formation.

Moreover, it is always a desire to discover new ancillary ligands, which upon coordination to a metal center will catalyze reactions differently from known ligand systems. This invention provides new ancillary ligands that may be used for coordination to a metal center or included in a composition with a metal or metal precursor compound. Upon coordination to the metal center or inclusion in the composition, such ligands influence the electronic and steric environment of the resulting coordination complex and may catalyze reactions differently, including more efficiently and selectively than known systems.

SUMMARY OF THE INVENTION

The invention disclosed herein is a new ligand, which can be characterized by the general formula:

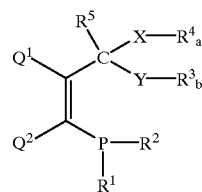

wherein
each $R^1$, $R^2$, $R^3$, $R^4$ and $R^5$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally, $R^1$ and $R^2$ are joined together in a ring structure and/or $R^3$ and $R^4$ are joined together in a ring structure;

$Q^1$ and $Q^2$ are, independently, selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally, $Q^1$ and $Q^2$ are joined together in a ring structure;

X is selected from the group consisting of C, H, O, P, Si, B and N atoms; and a is 0, 1, 2, or 3, depending on X;

Y is selected from the group consisting of N, P and O atoms; and b is 1 or 2, depending on Y; and C is a $sp^3$-hybridized carbon atom. In certain contexts, the inventive ligand is limited in that when Y is N and $Q^1$ and $Q^2$ are combined in a ring structure to form benzene with the backbone of the ligand, then $R^5$ is not hydrogen. These compounds may be optically active as a result of absolute stereochemical configuration at the $sp^3$-hybridized C atom and/or P atom and/or $R^3$ and/or $R^4$ substituents.

The ligands characterized by this formula can be included in a composition including a suitable metal or metal precursor compound, where the composition has catalytic properties. Also, the ligands can be coordinated with a metal precursor to form metal-ligand complexes, which may be catalysts. The metal-ligand complexes can be characterized by the general formula:

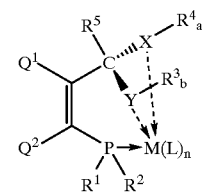

wherein
each $R^1$, $R^2$, $R^3$, $R^4$, $R^5$, $Q^1$, $Q^2$, C, X, Y, a and b are as defined above; and M is a transition metal selected from the group consisting of Groups 5, 6, 7, 8, 9 and 10 of the Periodic Table of Elements;

L is independently each occurrence, a neutral and/or charged ligand; and n is a number 0, 1, 2, 3, 4, and 5, depending on M.

These transition metal-ligand complexes or compositions catalyze reactions involving activation of and/or formation of H—Si, H—H, H—N, H—O, H—P, H—S, C—H, C—C, C═C, C≡C, C-halogen, C—N, C—O, C—S, C—P, and C—Si bonds. Specifically, such reactions include carbonylation, hydroformylation, hydroxycarbonylation, hydrocarbonylation, hydroesterification, hydrogenation, transfer hydrogenation, hydrosilylation, hydroboration, hydroamination, epoxidation, aziridation, reductive amination, C—H activation, insertion, C—H activation-insertion, C—H activation-substitution, C-halogen activation, C-halogen activation-substitution, C-halogen activation-insertion, cyclopropanation, alkene metathesis, polymerization, alkene oligomerization, alkene polymerization, alkyne oligomerization, alkyne polymerization, co-polymerization, CO-alkene co-oligomerization, CO-alkene co-polymerization, CO-alkyne co-oligomerization and CO-alkyne co-polymerization.

Thus, in one aspect of the invention, new ligands are provided that may be combined with or coordinated to transition metals or precursor compounds to provide useful catalysts.

In another aspect of this invention, new metal-ligand coordination complexes are provided that catalyze chemical reactions, including C—N bond formation.

In yet a further aspect of this invention, a C—N bond formation process is described employing the metal-ligand coordination complexes or compositions of this invention as a or the only component of a catalyst system.

In still a further aspect of this invention, new compounds may be created through the use of the metal-ligand coordination complexes or compositions of this invention as a or the only component of a catalyst system.

Further aspects of this invention will be evident to those of skill in the art upon review of this specification.

DETAILED DESCRIPTION OF THE INVENTION

The invention disclosed herein is a new ligand that may be combined with metals or metal precursor compounds to form coordination complexes or compositions of matter, which are useful as catalysts for chemical reactions.

As used herein, the phrase "characterized by the formula" is not intended to be limiting and is used in the same way that "comprising" is commonly used. The term "independently selected" is used herein to indicate that the R groups, e.g., $R^1$, $R^2$, $R^3$, $R^4$, and $R^5$ can be identical or different (e.g. $R^1$, $R^2$, $R^3$, $R^4$, and $R^5$ may all be substituted alkyls or $R^1$ and $R^2$ may be a substituted alkyl and $R^3$ may be an aryl, etc.). A named R group will generally have the structure that is recognized in the art as corresponding to R groups having that name. For the purposes of illustration, representative R groups as enumerated above are defined herein. These definitions are intended to supplement and illustrate, not preclude, the definitions known to those of skill in the art.

The term "alkyl" is used herein to refer to a branched or unbranched, saturated or unsaturated acyclic hydrocarbon radical. Suitable alkyl radicals include, for example, methyl, ethyl, n-propyl, i-propyl, 2-propenyl (or allyl), vinyl, n-butyl, t-butyl, i-butyl (or 2-methylpropyl), etc. In particular embodiments, alkyls have between 1 and 200 carbon atoms, between 1 and 50 carbon atoms or between 1 and 20 carbon atoms.

"Substituted alkyl" refers to an alkyl as just described in which one or more hydrogen atom to any carbon of the alkyl is replaced by another group such as a halogen, aryl, substituted aryl, cycloalkyl, substituted cycloalkyl, and combinations thereof. Suitable substituted alkyls include, for example, benzyl, trifluoromethyl and the like.

The term "heteroalkyl" refers to an alkyl as described above in which one or more hydrogen atoms to any carbon of the alkyl is replaced by a heteroatom selected from the group consisting of N, O, P, B, S, Si, Se and Ge. The bond between the carbon atom and the heteroatom may be saturated or unsaturated. Thus, an alkyl substituted with a heterocycloalkyl, substituted heterocycloalkyl, heteroaryl, substituted heteroaryl, alkoxy, aryloxy, boryl, phosphino, amino, silyl, thio, or seleno is within the scope of the term heteroalkyl. Suitable heteroalkyls include cyano, benzoyl, 2-pyridyl, 2-furyl and the like.

The term "cycloalkyl" is used herein to refer to a saturated or unsaturated cyclic non-aromatic hydrocarbon radical having a single ring or multiple condensed rings. Suitable cycloalkyl radicals include, for example, cyclopentyl, cyclohexyl, cyclooctenyl, bicyclooctyl, etc. In particular embodiments, cycloalkyls have between 3 and 200 carbon atoms, between 3 and 50 carbon atoms or between 3 and 20 carbon atoms.

"Substituted cycloalkyl" refers to cycloalkyl as just described including in which one or more hydrogen atom to any carbon of the cycloalkyl is replaced by another group such as a halogen, alkyl, substituted alkyl, aryl, substituted aryl, cycloalkyl, substituted cycloalkyl, heterocycloalkyl, substituted heterocycloalkyl, heteroaryl, substituted heteroaryl, alkoxy, aryloxy, boryl, phosphino, amino, silyl, thio, seleno and combinations thereof. Suitable substituted cycloalkyl radicals include, for example, 4-dimethylaminocyclohexyl, 4,5-dibromocyclohept-4-enyl, and the like.

The term "heterocycloalkyl" is used herein to refer to a cycloalkyl radical as described, but in which one or more or all carbon atoms of the saturated or unsaturated cyclic radical are replaced by a heteroatom such as nitrogen, phosphorous, oxygen, sulfur, silicon, germanium, selenium, or boron. Suitable heterocycloalkyls include, for example, piperazinyl, morpholinyl, tetrahydropyranyl, tetrahydrofuranyl, piperidinyl, pyrrolidinyl, oxazolinyl, and the like.

"Substituted heterocycloalkyl" refers to heterocycloalkyl as just described including in which one or more hydrogen atom to any atom of the heterocycloalkyl is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heterocycloalkyl radicals include, for example, N-methylpiperazinyl, 3-dimethylaminomorpholine, and the like.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone or oxygen as in diphenylether or nitrogen in diphenylamine. The aromatic ring(s) may include phenyl, naphthyl, biphenyl, diphenylether, diphenylamine and benzophenone among others. In particular embodiments, aryls have between 1 and 200 carbon atoms, between 1 and 50 carbon atoms or between 1 and 20 carbon atoms.

"Substituted aryl" refers to aryl as just described in which one or more hydrogen atom to any carbon is replaced by one or more functional groups such as alkyl, substituted alkyl, cycloalkyl, substituted cycloalkyl, heterocycloalkyl, substituted heterocycloalkyl, halogen, alkylhalos (e.g., $CF_3$), hydroxy, amino, phosphido, alkoxy, amino, thio and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone.

The term "heteroaryl" as used herein refers to aromatic rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more nonaromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Substituted heteroaryl" refers to heteroaryl as just described including in which one or more hydrogen atoms to any atom of the heteroaryl moiety is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heteroaryl radicals include, for example, 4-N,N-dimethylaminopyridine.

The term "alkoxy" is used herein to refer to the $—OZ^1$ radical, where $Z^1$ is selected from the group consisting of alkyl, substituted alkyl, cycloalkyl, substituted cycloalkyl, heterocylcoalkyl, substituted heterocycloalkyl, silyl groups and combinations thereof as described herein. Suitable alkoxy radicals include, for example, methoxy, ethoxy, benzyloxy, t-butoxy, etc. A related term is "aryloxy" where $Z^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

As used herein the term "silyl" refers to the $—SiZ^1Z^2Z^3$ radical, where each of $Z^1$, $Z^2$, and $Z^3$ is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein the term "boryl" refers to the $—BZ^1Z^2$ group, where each of $Z^1$ and $Z^2$ is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein, the term "phosphino" refers to the group $—PZ^1Z^2$, where each of $Z^1$ and $Z^2$ is independently selected from the group consisting of hydrogen, substituted or unsubstituted alkyl, cycloalkyl, heterocycloalkyl, heterocyclic, aryl, heteroaryl, silyl, alkoxy, aryloxy, amino and combinations thereof.

The term "amino" is used herein to refer to the group $—NZ^1Z^2$, where each of $Z^1$ and $Z^2$ is independently select from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "thio" is used herein to refer to the group $—SZ^1$, where $Z^1$ is selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "seleno" is used herein to refer to the group $—SeZ^1$, where $Z^1$ is selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "saturated" refers to lack of double and triple bonds between atoms of a radical group such as ethyl, cyclohexyl, pyrrolidinyl, and the like.

The term "unsaturated" refers to the presence one or more double and triple bonds between atoms of a radical group such as vinyl, acetylenyl, oxazolinyl, cyclohexenyl, acetyl and the like.

The ligands of this invention may be characterized by the general formula:

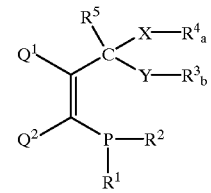

In this formula, each $R^1$, $R^2$, $R^3$, $R^4$ and $R^5$ are independently selected from the group consisting of hydrogen; alkyl, substituted alkyl, heteroalkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally, $R^1$ and $R^2$ are joined together in a ring structure, and optionally, $R^3$ and $R^4$ are joined together in a ring structure.

In more specific embodiments, $R^1$ and $R^2$ are independently selected from a group consisting of alkyl, substituted alkyl, heteroalkyl, cycloalkyl, substituted cycloalkyl, heterocycloalkyl, substituted heterocycloalkyl, aryl, substituted aryl, heteroaryl, substituted heteroaryl, alkyloxy, aryloxy, boryl, amino and silyl. Specific examples of $R^1$ and $R^2$ are methyl, ethyl, propyl, butyl, cyclopentyl, cylcohexyl, cyclooctyl, phenyl, naphthyl, benzyl, pyridyl, furyl, morpholino, methoxy, ethoxy, butoxy, phenoxy, benzyloxy, dimethylboryl, diphenylboryl, methylphenylboryl, dimethylamino, diethylamino, diphenylamino, dibenzylamino, trimethylsilyl, triethoxysilyl, triphenylsilyl, triphenoxysilyl, dimethyl-t-butylsilyl, and the like. In those embodiments where $R^1$ and $R^2$ are joined together in a ring structure, the ring (including $R^1$, $R^2$ and P) has from 3 to 15 non-hydrogen atoms as part of the backbone of the ring. Specific examples of $R^1$ and $R^2$ together are ethylene (giving a 3-membered ring), butylene (giving a 5-membered ring), bicyclooctyl, bicyclohexyl, 2,2'-biphenyl (giving a dibenzo fused 5-membered ring), 2,2'-binaphthyl (giving a dinaphtho fused 5-membered ring), 2,2'-biphenoxy (giving a 7-membered ring), 2,2'-dinaphthoxy (giving a 7-membered ring) and diethoxy (giving a 5-membered ring).

Also in more specific embodiments, each of $R^3$ and $R^4$ is, independently selected from the group consisting of alkyl, substituted alkyl, cycloalkyl, substituted cycloalkyl, heterocycloalkyl, substituted heterocycloalkyl, aryl, substituted aryl, heteroaryl, substituted heteroaryl and silyl. Specific examples of $R^3$ and $R^4$ are methyl, ethyl, propyl, butyl, cyclopentyl, cylcohexyl, cyclooctyl, phenyl, naphthyl, benzyl, trimethylsilyl, and the like. In those embodiments where $R^3$ and $R^4$ are joined together in a ring structure, the ring (including $R^3$, $R^4$, X, Y and C) has from 5 to 15 non-hydrogen atoms as part of the backbone of the ring. Specific examples of $R^3$ and $R^4$ together are ethylene (giving a 5-member ring), propylene (giving a 6-membered ring), 1,2-dioxybenzene (giving a 5-membered ring), 1,2-diaminobenzene (giving a 5-membered ring), 2,2'-biphenoxy (giving a 7-membered ring) and 2,2'-diaminobiphenyl (giving a 7-memebered ring).

More specifically, $R^5$ is selected from a group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkyloxy, aryloxy, amino, silyl, boryl, phosphino, thio, and seleno. Specific examples of $R^5$ are methyl, ethyl, propyl, butyl, cyclohexyl, cyclopropyl, cycloheptyl, t-butyl, phenyl, biphenyl, naphthyl, benzyl, pyridyl, furyl, quinolyl, morpholinyl, cyano, methoxy, ethoxy, t-butoxy, phenoxy, benzyloxy, dimethylamino, diethylamino, diphenylamino, phenylmethylamino, benzylmethylamino, trimethylsilyl, dimethyl-t-butylsilyl, triphenylsilyl, triethoxysilyl, dimethylboryl, diphenylboryl, diphenoxyboryl, 1,2-dioxyphenylboryl, 2,2'-biphenoxyboryl, 2,2'-dinaphthoxyboryl, diphenylphosphino, dibutylphosphino, dimethylphosphino, dicyclohexylphosphino, dicylcyclopentylphosphino, nitro, and methylphenylphosphino.

Each of $Q^1$ and $Q^2$ is independently selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, boryl, silyl, amino, phosphino, alkoxy, aryloxy, halogens, and combinations thereof. Specific examples of each of $Q^1$ and $Q^2$ are methyl, ethyl, propyl, butyl, phenyl, t-butyl, cyclohexyl, benzyl, acetyl, benzoyl, propionyl, pyridyl, morpholinyl, dimethylboryl, dibutylboryl, methylphenylboryl, diphenylboryl, trimethylsilyl, triphenylsilyl, dimethylphenylsilyl, dimethyl-t-butylsilyl, dimethylamino, diethylamino, methylphenylamino, benzylmethylamino, diphenylphosphino, dimethylphosphino, methylphenylphosphino, methoxy, phenoxy, benzyloxy, tetrahydropyranyl, chloro and bromo. Optionally, $Q^1$ and $Q^2$ are joined together in a ring structure. In those embodiments where $Q^1$ and $Q^2$ are joined together in a ring, the ring (including $Q^1$, $Q^2$ and the two carbon atoms in the backbone of the ligand) has from 4 to 10 non-hydrogen atoms in the backbone of the ring. Specific examples of ring are cyclohexene, cyclopentene, cyclobutene, cyclooctene, cyclopentadiene, naphthalene, anthracene, acridine, dihydrofuran, benzene, pyridine, oxazoline, furan, and thiophene.

In general, X is selected from the group consisting of C, H, O, P, Si, B and N atoms; and a is 0, 1, 2, or 3, depending on X. More specifically, X is selected from the group consisting of O and N.

Y is selected from the group consisting of N, P and O atoms; and b is 1 or 2, depending on Y.

C is a $sp^3$-hybridized carbon atom.

In a preferred embodiment, $Q^1$, $Q^2$ and the two carbon atoms in the backbone of the ligand form an aromatic group, such that the ligand can be characterized by the general formula:

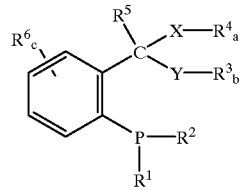

In this embodiment, $R^1$, $R^2$, $R^3$, $R^4$, $R^5$, X, Y, a, and b each have the definitions given above. In addition, $R^6$ is selected from the group consisting of electron withdrawing and electron donating groups and c is 0, 1, 2, 3 or 4. More specifically, of $R^6$ may be chosen from the group consisting of alkyl, substituted alkyl, cycloalkyl, substituted cycloalkyl, heterocycloalkyl, substituted heterocycloalkyl, aryl, substituted aryl, heteroaryl, substituted heteroaryl, silyl, amino, alkoxy, aryloxy, phosphino, boryl, transition metals, halogens and combinations thereof. Specific examples of $R^6$ include methyl, ethyl, propyl, t-butyl, phenyl, cyano, acetyl, benzoyl, nitro, dimethylamino, diethylamino, methylphenylamino, benzylmethylamino, trimethylsilyl, dimethylboryl, diphenylboryl, methylphenylboryl, dimethoxyboryl, chromium tricarbonyl, ruthenium tricarbonyl, and cyclopentadienyl iron. Optionally, two or more $R^6$ groups combine to form a fused ring structure with the aromatic group that forms a part of the ligand backbone. The additional fused ring may or may not contain a heteroatom. Examples of the aromatic group that is part of the backbone as combined with two or more $R^6$ groups that have formed a fused ring are nathphalene, quinoline, indole and the like. In connection with this preferred embodiment, when there is no $R^6$ and Y is N, then $R^5$ cannot be hydrogen.

The ligands are generally synthesized by addition of an organometal (e.g., n-BuLi) to a suitable starting substrate, followed by reaction with $R^1R^2PCl$. Alternatively, the ligands may be prepared by addition of $R^1R^2P$—M' (where M'=Li, K, Na) to a suitable starting substrate.

Once the desired ligand is formed, it may be combined with a metal atom, ion or other metal precursor compound. In many applications, the ligands of this invention will be combined with such a metal compound or precursor and the product of such combination is not determined, if a product forms. For example, the ligand may be added to a reaction vessel at the same time as the metal or metal precursor compound along with the reactants. The metal precursor compounds may be characterized by the general formula $M(L)_n$ where M is a metal selected from the group consisting of Groups 5, 6, 7, 8, 9 and 10 of the Periodic Table of Elements. In more specific embodiments, M is selected from the group consisting of V, Ta, Cr, W, Mo, Ru, Co, Ni, Pd, Fe, Mn, and Pt. L is a ligand ligand chosen from the group consisting of halide, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, hydroxy, boryl, silyl, hydrido, thio, seleno, phosphino, amino, and combinations thereof. When L is a charged ligand, L is selected from the group consisting of hydrogen, halogens, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof. When L is a neutral ligand, L is selected from the group consisting of carbon monoxide, isocyanide, nitrous oxide, $PA_3$, $NA_3$, $OA_2$, $SA_2$, $SeA_2$, and combinations thereof, wherein each A is independently selected from a group consisting of alkyl, substituted alkyl, heteroalkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, and amino. Specific examples of suitable metal precursor compounds include $Pd(dba)_2$ (dba=dibenzylydieneacteone), $Pd(OAc)_2$ (Ac=acetate) and the like. In this context, the ligand to metal precursor compound ratio is in the range of about 0.01:1 to about 100:1, more preferably in the range of about 0.5:1 to about 20:1.

In other applications, the ligand will be mixed with a suitable metal precursor compound prior to or simultaneous with allowing the mixture to be contacted to the reactants. When the ligand is mixed with the metal precursor compound a metal-ligand complex may be formed, which may be a catalyst.

In one form, the metal complexes may be characterized by the general formula:

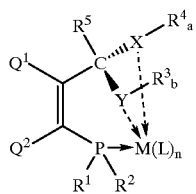

wherein
each $R^1$, $R^2$, $R^3$, $R^4$, $R^5$, $Q^1$, $Q^2$, C, X, Y, a and b are as defined above; and M is a transition metal selected from the group consisting of Groups 5, 6, 7, 8, 9 and 10 of the Periodic Table of Elements. In more specific embodiments, M is selected from the group consisting of V, Ta, Cr, W, Mo, Ru, Co, Ni, Pd, Fe, Mn and Pt.

L is independently each occurrence, a neutral and/or charged ligand. Generally, L is a ligand chosen from the group consisting of halide, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, hydroxy, boryl, silyl, hydrido, thio, seleno, phosphino, amino, and combinations thereof. When L is a charged ligand, L is selected from the group consisting of hydrogen, halogens, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof. When L is a neutral ligand, L is selected from the group consisting of carbon monoxide, isocyanide, nitrous oxide, $PA_3$, $NA_3$, $OA_2$, $SA_2$, $SeA_2$, and combinations thereof, wherein each A is independently selected from a group consisting of alkyl, substituted alkyl, heteroalkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, and amino.

n is the number 0, 1, 2, 3, 4, and 5. M can be neutral, cationic or anionic. The ligands of this invention bind to a metal via the P, X or Y atoms; optionally via P and Y atoms; optionally via only the P atom. Coordination modes described above may or may not depend on the nature of ligands L on the metal M, and for a given ligand L, the coordination modes may switch from one to another at different stages of a catalytic cycle.

In another form, the metal complexes may be characterized by the general formula:

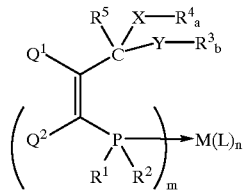

where in each $R^1$, $R^2$, $R^3$, $R^4$, $R^5$, $Q^1$, $Q^2$, C, X, Y, M, L, a, b and n are as defined above; and m is a number that is either 1, 2, 3 or 4.

These transition metal-ligand complexes catalyze reactions involving activation of and formation of bonds between H—Si, H—H, H—N, H—O, H—P, H—S, C—H, C—C, C=C, C≡C, C-halogen, C—N, C—O, C—S, C—P, and C—Si. Specifically, such reactions include carbonylation, hydroformylation, hydroxycarbonylation, hydrocarbonylation, hydroesterification, hydrogenation, hydrosilylation, hydroboration, hydroamination, epoxidation, aziridation, reductive amination, C—H activation, insertion, C—H activation-insertion, C—H activation-substitution, C-halogen activation, C-halogen activation-substitution, C-halogen activation-insertion, alkene metathesis, polymerization, alkene oligomerization, alkene polymerization, alkyne oligomerization, alkyne polymerization, co-polymerization, CO-alkene co-oligomerization, CO-alkene co-polymerization, CO-alkyne co-oligomerization and CO-alkyne co-polymerization. These reactions may occur at previously known conditions (or possibly novel conditions). Moreover, these reactions may be homogeneous or heterogeneous. In the case of heterogeneous reactions, the ligands may be supported, with or without the metal coordinated, on an organic or inorganic support. Suitable supports include silicas, aluminas, zeolites, polyethyleneglycols, polystyrenes, polyesters, polyamides, peptides and the like.

The ligands, metal-ligand coordination complexes and compositions of this invention can be prepared and tested for catalytic activity in one or more of the above reactions in a combinatorial fashion. Combinatorial chemistry generally involves the parallel or rapid serial synthesis and/or screening or characterization of compounds and compositions of matter. WO 96/11878 generally discloses combinatorial methods. The catalytic performance (activity and selectivity) of the ligands of this invention in combination with a suitable metal precursor or metal-ligand cordination complexes of this invention can be tested in a combinatorial and high thoughput fashion by employing thin layer chromatography (TLC) in combination with imaging technology. TLC is well known in the art, see for example Vol. 1, *Thin-Layer Chromatography, Reagents & Detection Methods,* Jork et al. (VCH Publishers, New York, N.Y. 1990). However, in the combinatorial catalysis context, it has not been previously described either alone or in combination with imaging technology as a rapid/high throughput screening method for determining reaction yields and hence catalyst performance. This screening technology allows for hundreds or thousands of potential catalysts to be tested in parallel for their effectiveness in causing the desired bond transformation.

More specifically, a rigid hemi-labile bidentate ligand containing P as one binding site and O as the other binding site with an aryl bridge was discovered via combinatorial catalysis for efficient Pd-catalyzed cross-coupling reaction of an arylbromide and a secondary amine to afford an arylamine. The ligand belongs to a new and previously undiscovered ligand class for efficient cross-coupling of an arylbromide with a secondary amine to afford an arylamine.

In a most preferred embodiment, the following ligand in combination with Pd(dba)$_2$ (where dba = dibenzylydieneacteone) was found to catalyze the reaction of an arylbromide with a secondary amine in high yield and with high selectivity:

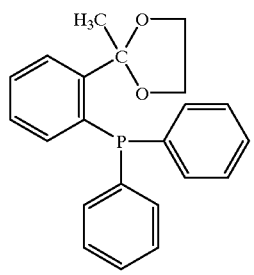

This ligand (referred to below as PCCCOO-1) cross coupled 4-bromobiphenyl with dibutylamine in the presence of NaO$^t$Bu at 100° C. in toluene to the desired 4-N,N-dibutylaminobiphenyl in a yield of 98% with 97% conversion of the starting 4-bromobiphenyl. In comparison, BINAP (binaphthalene) showed only 0.43% selectivity and a 77% conversion rate of the starting 4-bromobiphenyl material.

EXPERIMENTAL

Unless otherwise noted, all experiments were performed under an inert atmosphere of argon or nitrogen by using schlenk techniques. Anhydrous solvents in Sure-Seal® bottles, butyl lithium, aryl halides, secondary amines, sodium t-butoxide, cesium carbonate, Pd(dba)$_2$, Pd(OAc)$_2$, and ligand precursors were purchased from commercial sources and used as such.

EXAMPLE 1

This is an example of the synthesis of a ligand within the scope of this invention.

A solution of 2-bromoacetophenone (0.016 mol), ethylene glycol (0.024 mol), p-toluenesulphonic acid monohydrate (90 mg, catalytic amount) in toluene (50 mL) was refluxed for 12 hours using a Dean-Stark apparatus to remove the formed water. The reaction was cooled to room temperature and taken up in diethylether (100 mL). The ether extract was washed with water (3×25 mL), saturated NaCl solution (40 mL), and concentrated in vacuum. The crude product was rapidly column chromatographed using silica gel and hexane as eluent to afford the desired 2-bromoacetophenone-ketal (3.12 gm) which was used as such in the preparation of the ligand as described below.

To a solution of the 2-bromoacetophenone-ketal (0.011 mol) in anhydrous diethyl ether (25 mL) was added a solution of n-BuLi (0.011 mol) in hexane at −78° C. The reaction was stirred for 30 minutes at −78° C. and chlorodiphenylphosphine added slowly via syringe at −78° C. The reaction was stirred and allowed to warm up to room temperature overnight. The reaction was taken up in air free diethyl ether (100 mL), washed with an air-free solution of 10% NaOH in water, air-free water (25 mL), air-free saturated NaCl solution (25 mL), dried with K$_2$CO$_3$, and concentrated in vacuum to afford a yellowish solid. The yellowish solid was crystallized from ethanol to afford the PCCCOO-1 ligand (drawn above) as a off-white solid (2.2 gm).

$^{31}$P NMR (CDCl$_3$): ca. −10 ppm.

All rigid PCCCOO ligands in these examples were prepared using this procedure and starting with appropriate starting materials.

EXAMPLE 2

This is an example of the screening of a library of ligands in a combinatorial methodology using TLC as the high-throughput screen.

A mixture of aryl halide substrate (0.17 mmol), morpholine (0.19 mmol), sodium t-butoxide (0.19 mmol), palladium dibenzylidene acetone (0.0035 mmol), and ligand (0.0070 mmol) was loaded into each well (vessel) of a reaction block. 0.3 mL of reaction solvent (toluene or 1,4-dioxane) was added to each well and the reaction block was heated to ca. 100° C. for ca. 60 minutes. The reaction block was cooled to room temperature and identical amounts of reaction aliquot removed from each well into different microtiter plate wells and each aliquot diluted further by addition of 0.3 mL of dichloromethane. Identical aliquot from each of the diluted solutions were loaded on to a large TLC plate using capillaries and the TLC plate eluted using 4:1 hexane: EtOAc as the solvent system. After the elution, the TLC plate was irradiated with UV and the intensity of the individual desired product spots (corresponding to the aryl amine product) qualitatively analyzed as weak, medium, and strong. Alternatively, the intensity of the desired product spots on TLC can be quantitatively analyzed using a charge coupled device (CCD) digital camera/imaging technology to quantitatively afford the yield of the desired product directly. The identity of substrates and metal-ligand catalyst used in one of the discovery library, and the results of analysis are summarized in Table 1.

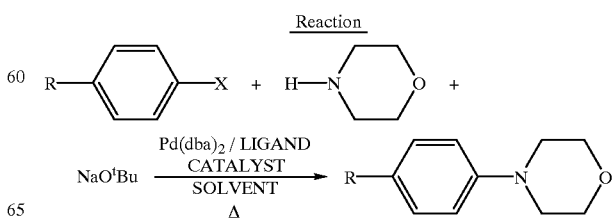

TABLE 1
| R = CF₃<br>X = Br | R = CF₃<br>X = Cl | R = CF₃<br>X = I | R = CF₃<br>X = Br | R = CF₃<br>X = Cl | R = CF₃<br>X = I | R = Ph<br>X = Br | LIGAND |
|---|---|---|---|---|---|---|---|
| ○ | ○ | ○ | ○ | ○ | ○ | ○ |  |
| ● | ▨ | ▨ | ● | ▨ | ● | ● | 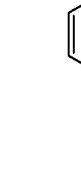 |
| ● | ▨ | ▨ | ● | ▨ | ● | ● | 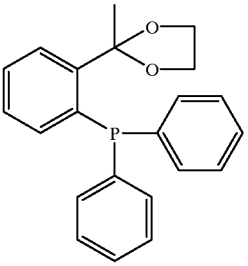 |
← Tol. → ← Diox. → → Tol.

TABLE 1-continued

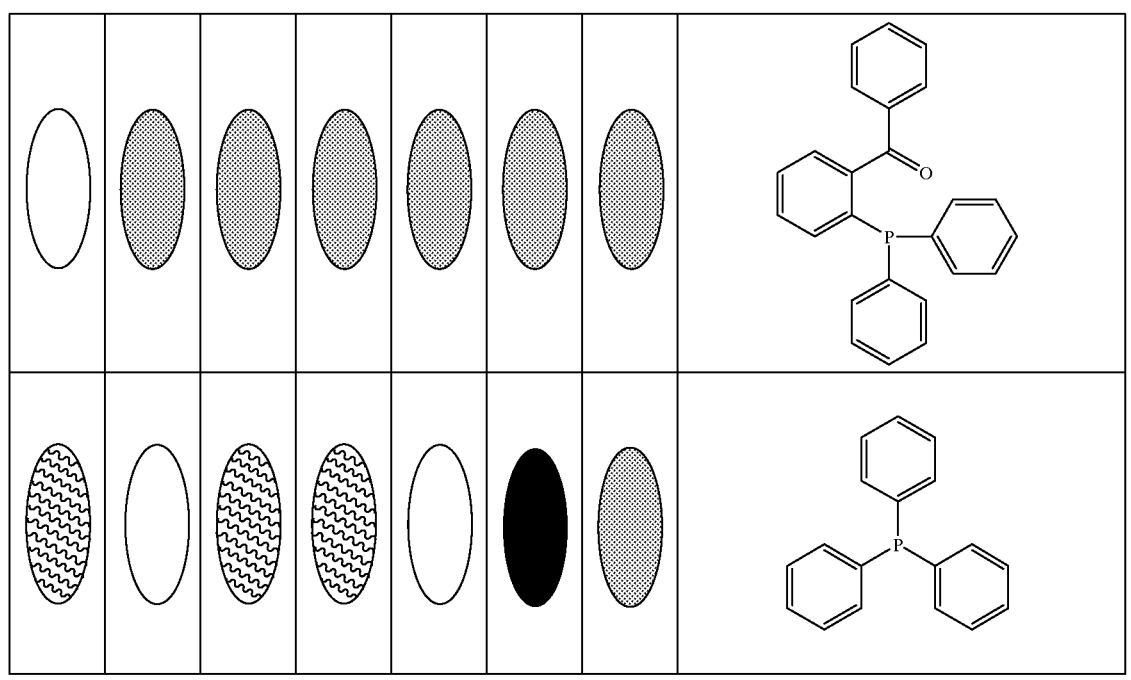

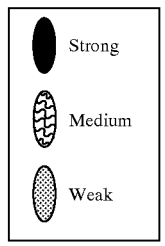

EXAMPLES 3–11

These are examples of individual catalyst screening: A reaction mixture containing 4-bromobiphenyl (1.1 mmol), secondary amine (1.3 mmol), sodium t-butoxide (1.3 mmol), Pd(dba)$_2$ (0.02 mmol), and ligand (0.04 mmol) in toluene was heated to 105–110° C. for about 50–90 minutes. The reaction mixture was cooled to room temperature and analyzed by gas chromatography-mass spectrometry (GCMS). The ligands, secondary amines and results are tabulated in the Table 2, below. Examples 10 and 11 are comparative examples of known catalyst systems generally used for this reaction.

| Example | Ligand | Amine | 4-Br-Biphenyl Conversion | Product Ratio (GCMS) Desired:Undesired |
|---|---|---|---|---|
| 3 | PCCCOO-1 | Morpholine | 100 | 49:1 |
| 4 | PCCCOO-1 | Dibutylamine | 97 | 98:1 |
| 5 | PCCCOO-2 | Dibutylamine | 85 | 23:1 |
| 6 | PCCCOO-3 | Morpholine | 95 | 12:1 |
| 7 | PCCCOO-3 | Dibutylamine | 100 | 2:1 |
| 8 | PCCCN | Morpholine | 100 | 99:1 |
| 9 | PCCCN | Dibutylamine | 24 | 4.8:1 |
| 10 | BINAP | Dibutylamine | 77 | 0.4:1 |
| 11 | P(o-toluyl)$_3$ | Morpholine | 100 | 13:1 |

PCCCOO-1 =

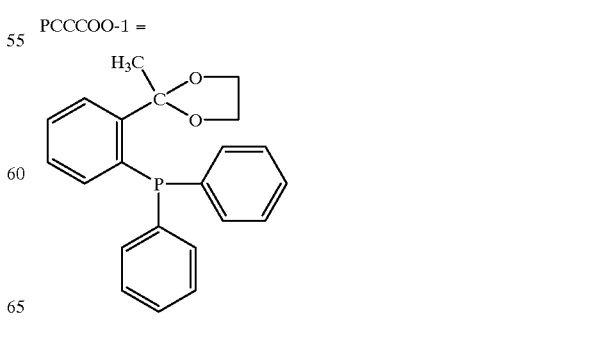

-continued

| Example | Ligand | Amine | 4-Br-Biphenyl Conversion | Product Ratio (GCMS) Desired:Undesired |
|---------|--------|-------|--------------------------|----------------------------------------|

PCCCOO-2 =

PCCCOO-3 =

PCCCN =

As is shown by Table 2 (by comparing Examples 3–7 to Examples 10–11), the PCCCOO ligands of this invention generally cross couple at a high conversion rate with a higher desired to undesired product ratio. For ligand PCCCN, this ligand was not previously known to catalyze this cross coupling reaction.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A compound characterized by the general formula:

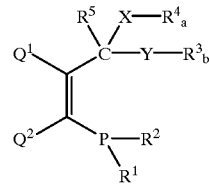

wherein
each $R^1$ and $R^2$ is independently selected from the group consisting of hydrogen, alkyl, substituted alkyl, cycloalkyl, substituted cycloalkyl, heteroalkyl, heterocycloalkyl, substituted heterocycloalkyl, heteroaryl, substituted heteroaryl, alkoxy, silyl, boryl, phosphino amino, thio, seleno, and combinations thereof;

each $R^3$, $R^4$ and $R^5$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino amino, thio, seleno, and combinations thereof; optionally, $R^1$ and $R^2$ are joined together in a ring structure and/or $R^3$ and $R^4$ are joined together in a ring structure;

each of $Q^1$ and $Q^2$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally $Q^1$ and $Q^2$ are joined together in a ring structure;

X is selected from the group consisting of C, H, O, P, B, Si, and N atoms; and a is 0, 1, 2, or 3, depending on X;

Y is selected from the group consisting of N, P and O atoms; and b is 1 or 2, depending on Y; and C is a $sp^3$-hybridized carbon atom, provided that when Y is N and $Q^1$ and $Q^2$ are joined in a ring structure with the two carbon atoms in the backbone of the ligand to form benzene, then $R^5$ is not hydrogen.

2. The compound of claim 1, wherein each of X and Y is independently selected from the group consisting of O, P, and N atoms.

3. The compound of claim 2, wherein each of X and Y are O.

4. The compound of claim 1, wherein when Y is selected from the group consisting of O, P and N, X is selected from the group consisting of C and H atoms.

5. The compound of claim 2, wherein each of $R^3$ and $R^4$ is independently selected from the group consisting of alkyl, substituted alkyl, heteroalkyl, cycloalkyl, substituted cycloalkyl, aryl and substituted aryl.

6. The compound of claim 2, wherein $R^3$ and $R^4$ are joined in a ring, wherein the said ring has between 5 and 10 non-hydrogen atoms.

7. The compound of claim 6, wherein said ring has between 5 and 6 non-hydrogen atoms in the backbone of the ring.

8. The compound of claim 7, wherein said ring consists of X, C, Y, $R^3$ and $R^4$, wherein $R^3$ and $R^4$ together are ethylene or propylene.

9. The compound of claim 1, wherein each of $Q^1$ and $Q^2$ is independently selected from a group consisting of alkyl, substituted alkyl, heteroalkyl, cycloalkyl, substituted cycloalkyl, aryl, substituted cycloalkyl, heteroaryl, substituted heteroaryl, cyano, nitro, and carbonyl.

10. The compound of claim 9, wherein $Q^1$ and $Q^2$ are joined in a ring structure, wherein the said ring structure has between 5 and 10 non-hydrogen atoms in the backbone of the ring.

11. The compound of claim 10, wherein the said ring structure is benzene.

12. The compound of claim 1 wherein each $R^1$ and $R^2$ is independently selected from the group consisting of alkyl, substituted alkyl, cycloalkyl, substituted cycloalkyl, heteroalkyl, heteroaryl, substituted heteroaryl, alkoxy, amino and silyl.

13. The compound of claim 12, wherein each $R^1$ and $R^2$ is independently selected from the group consisting of alkyl and cycloalkyl.

14. The compound of claim 13, wherein $R^1$ and $R^2$ are cyclohexyl.

15. The compound of claim 1, wherein $R^5$ is selected from the group consisting of hydrogen, alkyl, substituted alkyl, heteroalkyl, cycloalkyl, substituted cycloalkyl, aryl, substituted aryl, heteroaryl, substituted heteroaryl, cyano, alkoxy, aryloxy, amino, silyl, boryl, phosphino, thio, nitro and combinations thereof.

16. The compound in claim 1, wherein in the said compound is optically active as a result of absolute stereochemical configuration at the sp$^3$-hybridized C atom or P atom or $R^3$ or $R^4$ substituents.

17. A complex characterized by the general formula:

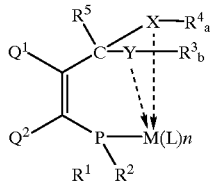

wherein
each $R^1$, $R^2$, $R^3$, $R^4$ and $R^5$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino amino, thio, seleno, and combinations thereof; optionally, $R^1$ and $R^2$ are joined together in a ring structure and/or $R^3$ and $R^4$ are joined together in a ring structure;

each of $Q^1$ and $Q^2$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally $Q^1$ and $Q^2$ are joined together in a ring structure;

X is selected from the group consisting of C, H, O, P, B, Si, and N atoms and may or may not interact with the metal center M; and a is 0, 1, 2, or 3, depending on X;

Y is selected from the group consisting of N, P and O atoms and may or may not interact with the metal center M; and b is 1 or 2, depending on Y; and C is a sp$^3$-hybridized carbon atom, M is a transition metal selected from the group consisting of Groups 5, 6, 9 and 10 of the Periodic Table of the Elements, iron, osmium, manganese, and technetium;

L is independently each occurrence, selected from the group consisting of hydrogen, alkyl, substituted alkyl, cycloalkyl, substituted cycloalkyl, heteroalkyl, heterocycloalkyl, substituted heterocycloalky aryl, substitiuted aryl, heteroaryl, substituted heteroaryl, alkoxy, aryloxy, silyl, boryl, phosphino, amino, thio, seleno, and combinations thereof; and n is a number 0, 1, 2, 3, 4, and 5, depending on M.

18. The complex of claim 17, wherein M is selected from the group consisting of Pd, Ni, Co, Fe, Rh, Ir, Pt, Cr, Mo, Mn, and V.

19. The complex of claim 18 wherein M is selected from the group consisting of Pd, Ni, Fe, Ir, Pt, and Rh.

20. The complex of claim 17, wherein L is selected from the group consisting of carbon monoxide, isocyanide, nitrous oxide, $PA_3$, $NA_3$, $OA_2$, $SA_2$, $SeA_2$, and combinations thereof, wherein each A is independently selected from a group consisting of alkyl, substituted alkyl, heteroalkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, and amino.

21. The complex of claim 17, wherein X and Y are selected from the group consisting of O, P, and N.

22. The complex of claim 21, wherein X and Y are both O.

23. The complex of claim 19, wherein when Y selected from the group consisting of O, P and N, X is selected from the group consisting of C and H atoms.

24. The complex of claim 19, wherein each of $R^3$ and $R^4$ is independently selected from the group consisting of alkyl, substituted alkyl, cycloalkyl, substituted cycloalkyl, aryl and substituted aryl.

25. The complex of claim 24, wherein $R^3$ and $R^4$ are joined in a ring, wherein the said ring has between 5 and 10 non-hydrogen atoms.

26. The complex of claim 25, wherein said ring has between 5 and 6 non-hydrogen atoms in the backbone of the ring.

27. The complex of claim 26, wherein said ring consists of X, C, Y, $R^3$ and $R^4$, wherein $R^3$ and $R^4$ together are ethylene or propylene.

28. The complex of claim 17, wherein each of $Q^1$ and $Q^2$ is independently selected from a group consisting of alkyl, substituted alkyl, heteroalkyl, cycloalkyl, substituted cycloalkyl, aryl, substituted cycloalkyl, heteroaryl, substituted heteroaryl, cyano, nitro, and carbonyl.

29. The complex of claim 28, wherein $Q^1$ and $Q^2$ are joined in a ring structure, wherein the said ring structure has between 5 and 10 non-hydrogen atoms in the backbone of the ring.

30. The complex of claim 29, wherein the said ring structure is benzene.

31. The complex of claim 17, wherein each of $R^1$ and $R^2$ is independently selected from the group consisting of alkyl substituted alkyl, cycloalkyl, substituted cycloalkyl, heteroalkyl, aryl, substitute aryl, heteroaryl, substituted heteroaryl, alkoxy, aryloxy, amino and silyl.

32. The complex of claim 31, wherein each $R^1$ and $R^2$ is independently selected from the group consisting of alkyl, aryl and cycloalkyl.

33. The complex of claim 32, wherein $R^1$ and $R^2$ is independently selected from the group consisting of phenyl and cyclohexyl.

34. The complex of claim 17, wherein $R^5$ is selected from the group consisting of hydrogen, alkyl, substituted alkyl, heteroalkyl, cycloalkyl, substituted cycloalkyl, aryl, substituted aryl, heteroaryl, substituted heteroaryl, cyano, alkoxy, aryloxy, amino, silyl, boryl, phosphino, thio, nitro and combinations thereof.

35. The complex in claim 17, wherein in the said compound is optically active as a result of absolute stereochemical configuration at the sp³-hybridized C atom and/or P atom and/or R³ and/or R⁴ substituents.

36. A composition of matter comprising the compound of claim 1 and a metal precursor characterized by the general formula $M(L)_n$, where M is a transition metal selected from the group consisting of Groups 5, 6, 9, and 10 of the Periodic Table of the Elements, iron, osmium, manganese and technetium; L is independently each occurrence, selected from the group consisting of hydrogen, alkyl, substituted alkyl, cycloalkyl, substituted cycloalkyl, heteroalkyl, heterocycloalkyl, substituted heterocycloalky aryl, substitiuted aryl, heteroaryl, substituted heteroaryl, alkoxy, aryloxy, silyl, boryl, phosphino, amino, thio, seleno, and combinations thereof; and n is a number 0, 1, 2, 3, 4, and 5.

37. The composition of claim 36 wherein the ratio of compound to metal precursor is in the range of about 0.01:1 to about 100:1.

38. The composition of claim 37 wherein the ratio of compound to metal precursor is in the range of about 0.5:1 to about 20:1.

39. The composition of claim 36, wherein the compound is of claim 2.

40. The composition of claim 36, wherein the compound is of claim 3.

41. The composition of claim 36, wherein the compound is of claim 4.

42. The composition of claim 36, wherein the compound is of claim 8.

43. The composition of claim 36, wherein the compound is of claim 10.

44. The composition of claim 36, wherein the compound is of claim 14.

45. A process comprising contacting the complex in claim 17 with a compound to form a C—H, C—C, C—N, C—O, C—S, C—P, C—B, and C—Si bond.

46. The process of claim 45, wherein C—H, C—C, C—N, C—O, C—S, C—P, C—B, and C—Si bond formation involves a sp²-hybridized C atom.

47. The process of claim 46, wherein the processes involve carbonylation, hydroformylation, hydroxycarbonylation, hydrocarbonylation, hydroesterification, hydrogenation, hydrosilylation, hydroboration, hydroamination, epoxidation, aziridation, reductive amination, C—H activation, insertion, C—H activation-insertion, C—H activation-substitution, C-halogen activation, C-halogen activation-substitution, C-halogen activation-insertion, alkene metathesis, polymerization, alkene oligomerization, alkene polymerization, alkyne oligomerization, alkyne polymerization, co-polymerization, CO-alkene co-oligomerization, CO-alkene co-polymerization, CO-alkyne co-oligomerization, and CO-alkyne co-polymerization.

48. A process to aminate comprising contacting an amine and a composition to be aminated with a compound characterized by the formula:

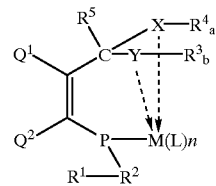

wherein each $R^1, R^2, R^3, R^4$ and $R^5$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino amino, thio, seleno, and combinations thereof; optionally, $R^1$ and $R^2$ are joined together in a ring structure and/or $R^3$ and $R^4$ are joined together in a ring structure;

each of $Q^1$ and $Q^2$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally $Q^1$ and $Q^2$ are joined together in a ring structure;

X is selected from the group consisting of C, H, O, P, B, Si, and N atoms and may or may not interact with the metal center M; and a is 0, 1, 2, or 3, depending on X;

Y is selected from the group consisting of N, P and O atoms and may or may not interact with the metal center M; and b is 1 or 2, depending on Y; and C is a sp³-hybridized carbon atom, M is a transition metal selected from the group consisting of Groups 5, 6, 7, 8, 9 and 10 of the Periodic Table of the Elements;

L is independently each occurrence, selected from the group consisting of hydrogen, alkyl, substituted alkyl, halogen, cycloalkyl, substituted cycloalkyl, heteroalkyl, heterocycloalkyl, substituted heterocycloalky aryl, substitiuted aryl, heteroaryl, substituted heteroaryl, alkoxy, aryloxy, silyl, boryl, phosphino, amino, thio, seleno, and combinations thereof; and n is a number 0, 1, 2, 3, 4, and 5, depending on M.

49. The process of claim 48, wherein each of X and Y is independently selected from the group consisting of O, P, and N atoms.

50. The process of claim 49, wherein each of X and Y are O.

51. The process of claim 48, wherein when Y is selected from the group consisting of O, P and N, X is selected from the group consisting of C and H atoms.

52. The process of claim 49, wherein each of $R^3$ and $R^4$ is independently selected from the group consisting of alkyl, substituted alkyl, heteroalkyl, cycloalkyl, substituted cycloalkyl, aryl and substituted aryl.

53. The process of claim 49, wherein $R^3$ and $R^4$ are joined in a ring, wherein the said ring has between 5 and 10 non-hydrogen atoms.

54. The process of claim 53, wherein said ring has between 5 and 6 non-hydrogen atoms in the backbone of the ring.

55. The process of claim 48, wherein each of $Q^1$ and $Q^2$ is independently selected from a group consisting of alkyl, substituted alkyl, heteroalkyl, cycloalkyl, substituted cycloalkyl, aryl, substituted cycloalkyl, heteroaryl, substituted heteroaryl, cyano, nitro, and carbonyl.

56. The process of claim 55, wherein the said ring structure is benzene.

57. The process of claim 55, wherein each $R^1$ and $R^2$ is independently selected from the group consisting of alkyl, aryl and cycloalkyl.

58. A method for determining in a parallel fashion whether a desired chemical reaction has occurred by using thin layer chromatography in combination with imaging technology as a high-throughput screen.

59. The method of claim 58 wherein said determination is qualitative.

60. The method of claim 58 wherein said determination is quantitative.

61. The method of claim 60 wherein the imaging technology is a charge coupled device camera.

62. A metal complex characterized by the general formula:

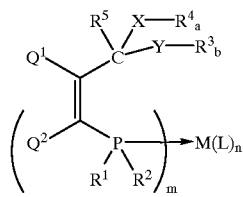

wherein
each $R^1$, $R^2$, $R^3$, $R^4$ and $R^5$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally, $R^1$ and $R^2$ are joined together in a ring structure and/or $R^3$ and $R^4$ are joined together in a ring structure;

each of $Q^1$ and $Q^2$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally, $Q^1$ and $Q^2$ are joined together in a ring structure;

X is selected from the group consisting of C, H, O, P, Si, B and N; and a is 0, 1, 2, or 3, depending on X;

Y is selected from the group consisting of N, P and O; and b is 1 or 2, depending on Y;

C is a $sp^3$-hybridized carbon atom;

M is a transition metal selected from the group consisting of Groups 5, 6, 7, 8, 9 and 10 of the Periodic Table of Elements;

L is independently each occurrence, a ligand;

n is a number 0, 1, 2, 3, 4, and 5; and m is a number 1, 2, 3 or 4.

* * * * *

UNITED STATES PATENT AND TRADEMARK OFFICE
CERTIFICATE OF CORRECTION

PATENT NO.    : 6,225,487 B1
DATED         : May 1, 2001
INVENTOR(S)   : Guram, Anil It is certified that error appears in the above-identified patent and that said Letters Patent is hereby corrected as shown below:

Column 20,
Line 4, the word "heterocycloalky" should be replaced with -- heterocycloalkyl, --
Line 54, a comma should be inserted after the word "alkyl"

Column 21,
Line 15, the word "heterocycloalky" should be replaced with -- heterocycloalkyl, --

Column 22,
Line 44, the word "cloalky" should be replaced with -- cloalkyl, --

Column 24,
Line 8, "Q" should be replaced with -- $Q^1$ --

Signed and Sealed this

Eighteenth Day of February, 2003

JAMES E. ROGAN
*Director of the United States Patent and Trademark Office*